United States Patent [19]

Vlock

[11] Patent Number: 4,915,272
[45] Date of Patent: Apr. 10, 1990

[54] GLOVE DONNING AND REMOVING MACHINE

[75] Inventor: Richard S. Vlock, Gloversville, N.Y.

[73] Assignees: David G. Vlock; Lawrence Rosen, both of New York, N.Y.

[21] Appl. No.: 218,646

[22] Filed: Jul. 13, 1988

[51] Int. Cl.$^4$ ............................................. A47G 25/90
[52] U.S. Cl. ........................................ 223/111; 312/1; 206/278
[58] Field of Search ........................... 223/111; 312/1; 206/278, 438; 2/168, DIG. 7

[56] References Cited

U.S. PATENT DOCUMENTS

| | | | |
|---|---|---|---|
| 1,938,685 | 12/1933 | Breuls et al. | 223/111 |
| 1,996,377 | 4/1935 | Hinchen | 223/111 |
| 2,741,410 | 4/1956 | Violette | 223/111 |
| 3,067,001 | 12/1962 | McCollum | 223/111 X |
| 3,237,821 | 3/1966 | Hayne et al. | 223/111 |
| 3,323,846 | 6/1967 | Boddy | 312/1 |
| 3,695,493 | 10/1972 | Karr | 223/111 |
| 4,002,276 | 1/1977 | Poncy et al. | 223/111 |
| 4,155,494 | 5/1979 | Poncy et al. | 223/111 |
| 4,275,812 | 6/1981 | Poncy et al. | 206/278 |

Primary Examiner—Werner H. Schroeder
Attorney, Agent, or Firm—Ostrolenk, Faber, Gerb & Soffen

[57] ABSTRACT

A glove donning and removing machine includes a pair of glove donning cylinders in which a negative pressure is created to inflate gloves mounted to the rims of the cylinders. This enables a person to insert his/her hands simultaneously in both gloves. The glove donning cylinders are selectively pivotable toward and away from the user and are also rotatable, allowing for fully adjustable orienting of the cylinders and of the gloves mounted to the cylinders. Actuating switches for controlling inflating and deflating of the gloves are located within the cylinders for allowing manipulation of the switches from within the glove inflating cylinders. Separately of the glove donning cylinders, a pair of glove removing cylinders are provided for removing a pair of gloves from a person's hands. According to one embodiment, trapezoid shaped resiliently mounted segments, disposed at the opening into the glove removing cylinders, serve to snag the cuff portion of a glove and to thus pull the gloves off a person's hands. According to another embodiment, each of the glove removing cylinders comprises an outer cylinder, a perforated hand form within the outer cylinder and a suction pump for creating a negative pressure within the outer cylinder. When a gloved hand is inserted in the hand form the glove is sucked away from the hand against the interior wall of the hand form allowing the hand to be withdrawn without the glove.

35 Claims, 6 Drawing Sheets

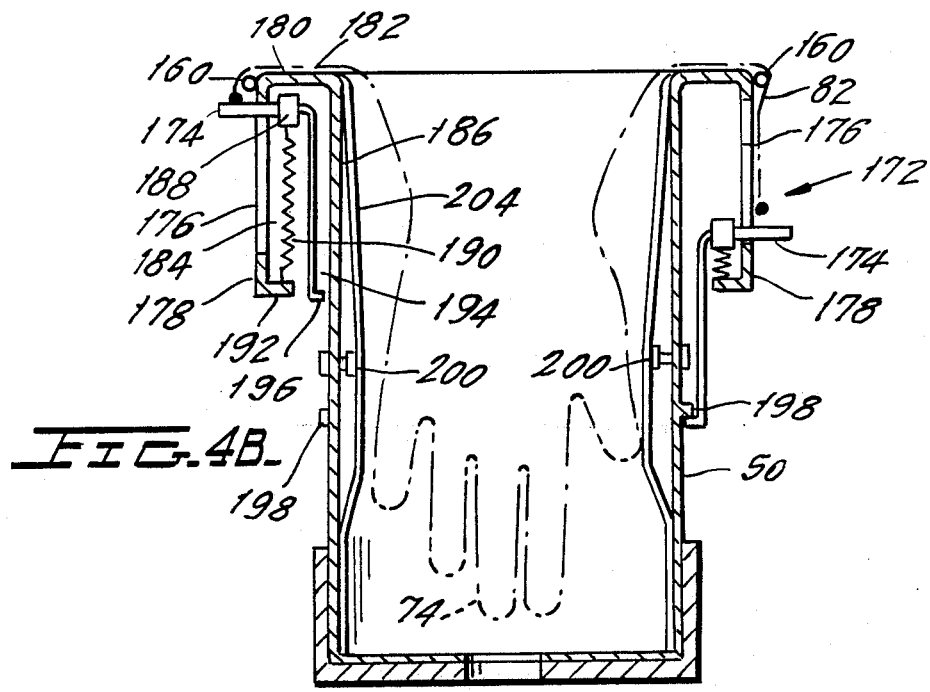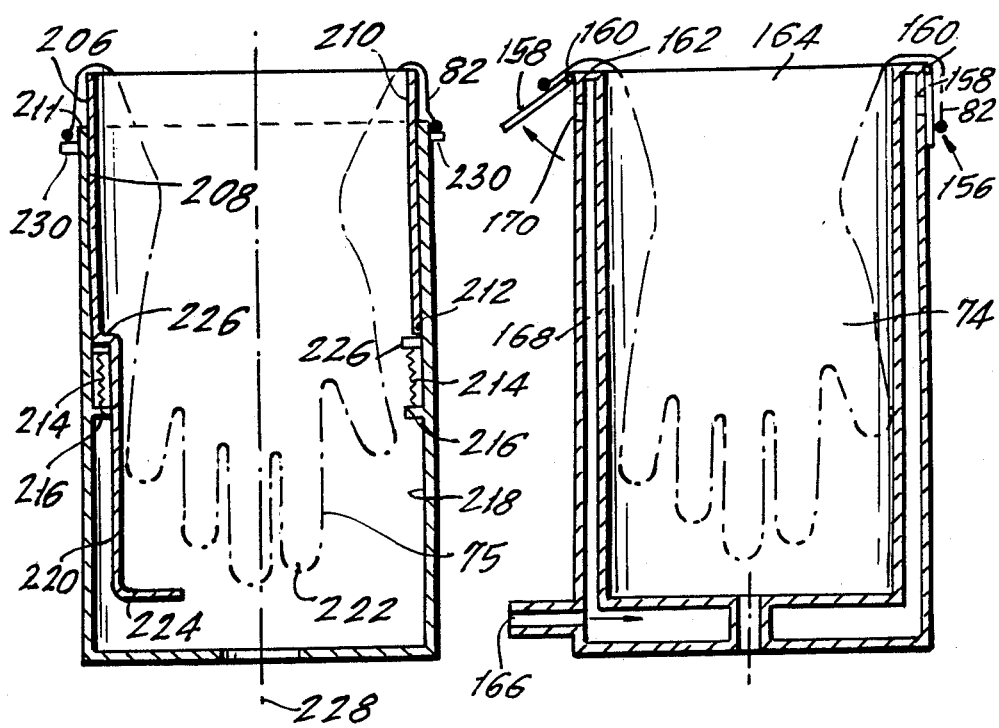

GLOVE DONNING AND REMOVING MACHINE

BACKGROUND OF THE INVENTION

The present invention relates to a glove donning and removing machine, and more particularly to a glove donning and removing machine for enabling a person to don or remove a pair of gloves simultaneously, easily and without assistance from another person.

The fear of spreading disease and the AIDS epidemic in particular have created a crisis atmosphere and a heightened awareness of the necessity to wear puncture free, perfect gloves during any medical procedure. The importance of donning gloves and exchanging gloves on the slightest suspicion that they may have been damaged in use cannot be overemphasized. It is life threatening to ignore the risk of transferring body fluids, such as blood or the like, from one person to another.

Unfortunately, gloves which interfere minimally with finger sensitivity, for example, gloves fabricated of rubber, latex or similar materials, are the only ones which are practical for medical applications. But because such gloves must be tightly fitted to obtain good finger sensitivity, the gloves are prone to tearing both while they are being donned or during use. It is therefore imperative, in order to overcome the natural human tendency to become careless, that glove donning and removing be made exceedingly simple, easy and rapid.

Methods and machines for applying or removing gloves have been described in the art, including in several United States patents. For example, U.S. Pat. No. 1,996,377 describes a glove donning machine with a glove inflating chamber. The glove is mounted such that it hangs into the chamber with the cuff portion of the glove stretched wide and fitted on a rim at the opening into the glove inflating chamber. Thereafter a negative pressure is created within the chamber, causing the glove to expand larger than the size of a human hand by atmospheric air rushing into the glove.

In the U.S. Pat. No. 1,996,377, a suction pump is used for creating the negative pressure and a movable collar at the rim of the inflating chamber helps to dislodge the cuff of the glove from the rim after a person has inserted his/her hand into the glove. When the negative pressure in the chamber is released, the glove shrinks and encases the hand of the person.

U.S. Pat. No. 3,695,493 describes a similar glove donning machine which permits donning of gloves without touching of the exterior surfaces of the gloves by bare hands. A negative pressure is created in a glove inflating chamber by a bellows assembly 30.

U.S. Pat. No. 4,002,276 discloses a glove donning chamber formed by a pair of telescoping cylinders. Relative retraction of the cylinders away from one another creates a negative pressure which inflates the glove, as in the above patents. Subsequent inward pushing of the retracted cylinders is designed to create a positive pressure which is alleged to be sufficient for exploding the cuff of the glove off the rim of the cylinder and onto a person's wrist.

In all known devices, the axial orientation of the glove inflating chambers is not adjustable. In several machines the chamber axis is upright, requiring vertical and, therefore, cumbersome moving of one's hand during glove donning. While other machines provide more comfortable tilted chambers, machines providing individually adjustable chamber orientation are not known in the art.

Also, once a glove is mounted to the rim of any of the prior art glove donning machines, the position of the glove on the rim is fixed. It is impossible to rotate either the glove or the chamber to orient the thumb and fingers of the glove to the most convenient position, except by removing and remounting of the glove. This is bothersome, particularly if machines are to include dual cylinders for simultaneous donning of a pair of gloves.

Another disadvantage of the known glove donning machines arises from their use of only externally located switches or a foot pedal for controlling glove inflating and glove deflating. Foot pedals are cumbersome and difficult to use, particularly when they have several sections for controlling more than one machine function. In the case of hand actuated switches, simultaneous donning of a pair of gloves is impossible because one hand must remain free for actuating the switches. When the gloves are donned serially, the first gloved hand necessarily must contact the switches during donning of the second glove, which is undesirable.

SUMMARY OF THE INVENTION

Accordingly, it is an object of the present invention to provide a glove donning and removing machine which is simple and inexpensive to manufacture.

It is a another object of the invention to provide a glove donning machine which is simple and easy to use.

It is a further object of the invention to provide a glove donning machine for donning a pair of gloves simultaneously.

It is still a further object of the invention to provide a glove donning machine having dual glove inflating cylinders wherein the cylinders are tiltable relative to the user to enable a user to select a most comfortable cylinder position.

It is yet another object of the invention to provide a glove donning machine having glove inflating cylinders which are rotatable to allow adjusting of the finger and thumbs orientation of the glove after the glove has been mounted to the cylinders.

It is yet another object of the invention to provide a glove donning machine which is operable by the user from within the cylinders during glove donning.

The foregoing and other objects of the invention are realized by means of a glove donning machine which includes a pair of glove inflating cylinders each of which has a hand insertion opening and a rim at the hand insertion opening for mounting the cuff portion of a glove thereon.

A suction pump or a similar mechanism is provided for producing a negative pressure in the cylinder to inflate the glove to allow a person to insert his/her hand into the inflated glove. Subsequent restoring of ambient pressure conditions within the cylinders results in the shrinking of the gloves about the person's hands.

Preferably, the cylinders are mounted adjustably such that they may be pivoted toward and away from the user and rotated to allow a user to orient the thumb and finger portions of the glove mounted to the cylinders.

The present invention provides several mechanisms for dislodging the cuff portions of the gloves from the rims of the cylinders after the glove has shrunk about the person's hand. In one embodiment, a positive pressure is produced within the cylinders to explode the cuff portions off the rim. In another embodiment, an axially movable pin is provided for dislodging the cuff portions off the rims of the cylinders. In yet another embodiment, pivotable rods at the rims of the cylinder swing radially out in response to a blast of air to dislodge the cuff portions. As still further embodiment provides a movable rim structure at the opening into each cylinder. The cuff portion is mounted to the movable rim and—to dislodge the cuff portion—the movable rim can be pulled with one's hand deeper into the cylinder to thereby force the glove off the rim.

The invention also provides a special glove assembly in which a glove is preassembled on an expansion ring. The ring with the glove is designed to be simply fitted to the opening of the cylinder. Thereby the effort and time required to mount the cuff portion of a glove to the rim of a cylinder is dispensed with. Preferably, the ring of the glove assembly includes projecting pins which, when the ring is mounted to the cylinder, serve to actuate switches located at the rim of the cylinder to automatically start inflating of the glove.

Still further, the invention also provides actuating switches that are disposed and operable from within the cylinders to allow controlling of the inflating and deflating of gloves from within the glove inflating cylinders.

The invention also provides glove removing cylinders for allowing a person to simultaneously remove a pair of gloves. In a first embodiment, the glove removing cylinders have trapezoid shaped segments at the opening into the cylinders which snag the cuff portion of a glove and allow the gloves to be removed as a person withdraws his hands from the cylinders.

In accordance with a second embodiment, each of the glove removing cylinders is comprises of an outer cylinder and a perforated hand form disposed within the outer cylinder. A negative pressure created within the outer cylinder communicates into the hand form and causes the glove on the hand of the person that had been inserted into the hand form to be sucked against the interior wall of the hand form. The person is then able to withdraw his hand from the cylinder, leaving the glove behind.

Other features and advantages of the present invention will become apparent from the following description of the invention which refers to the accompanying drawings.

BRIEF DESCRIPTION OF THE DRAWINGS

FIG. 4A is a cross-section through a second cuff dislodging embodiment in accordance with the present invention.

FIG. 4B is a cross-section through a third cuff dislodging embodiment of the present invention.

FIG. 4C is a cross-section through a further embodiment of a glove cuff dislodging mechanism.

DETAILED DESCRIPTION OF PREFERRED EMBODIMENTS

Figure 1:
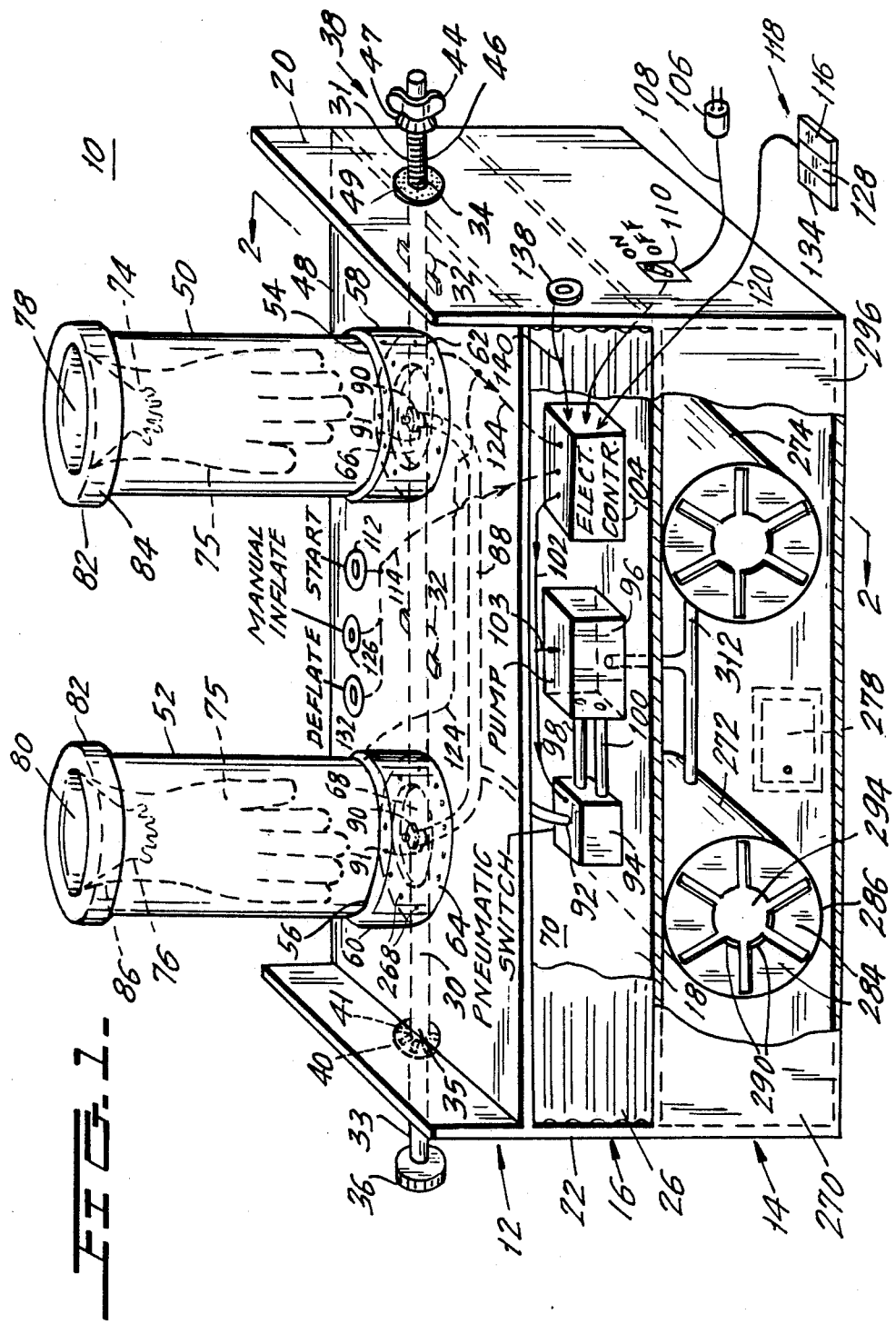
FIG. 1 is a perspective of a glove donning and removing machine in accordance with the present invention.

FIG. 1 illustrates a dual cylinder glove donning and removing machine 10 for simultaneous donning or removing of a pair of gloves. The machine 10 includes an upper housing supporting a glove donning system 12 and a lower housing which holds a glove removing system 14. While in FIG. 1 the systems 12 and 14 are mounted atop one another to permit sharing of components, it is possible and within the spirit of the invention for each of the two systems 12 and 14 to be self-contained and provided separately of one another.

Figure 2:
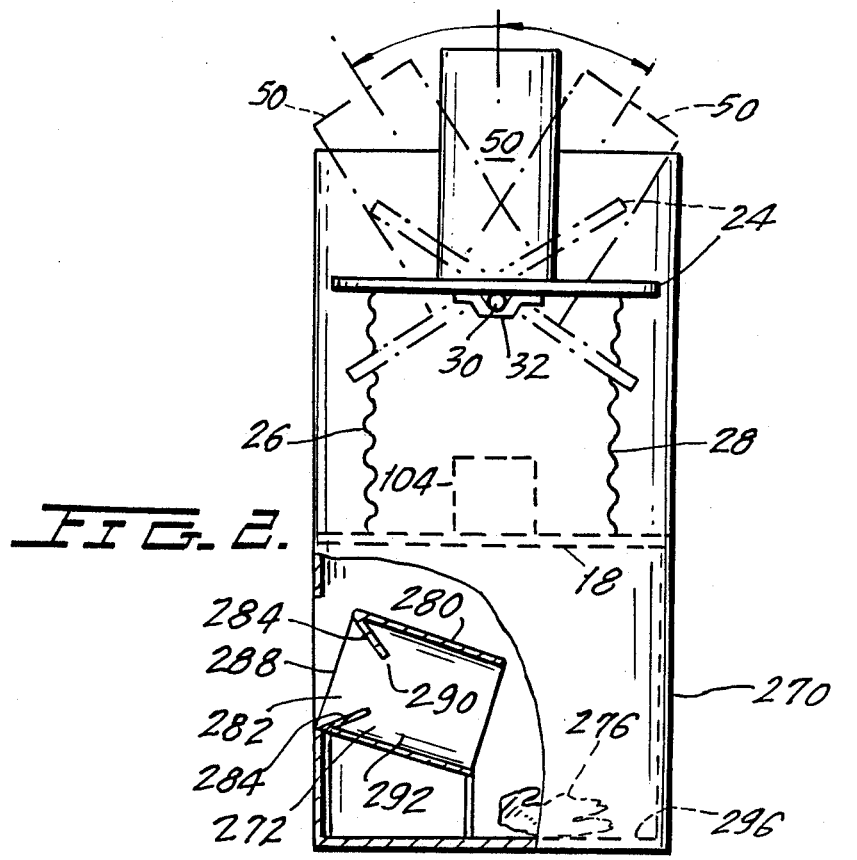
FIG. 2 is a cross-section through line 2—2 in FIG. 1.

The glove donning system 12 of machine 10 includes a hardware enclosure 16 which is defined by a horizontally extending base 18, a first upright panel 20 at the right side of base 18, a second upright panel 22 at the left side of base 18, a generally horizontally extending pivotable platform 24 above the base 18, and front and rear flexible walls 26 and 28 for enclosing the front and back sides of hardware enclosure 16. The flexible walls 26 and 28 allow the platform 24 to pivot to the front or the back as shown in FIG. 2.

The platform 24 is secured to a pivoting rod 30, by several U-shaped bolts 32 or by any securing means, in a manner that allows the platform 24 to pivot and assume various desired orientations by rotating and then locking the rod 30. To this end, the right end 31 of the rod 30 extends through a circular hole 34 in the right upright panel 20 and the left end 33 thereof extends similarly through a circular opening 35 in the left upright panel 22. To set a desired platform position, the rod 30 may be grasped and rotated by means of the knurled knob 36 and thereafter locked by tightening the locking mechanism 38, disposed at the right end 31 of the 30.

The locking mechanism 38 can be embodied in many different forms. In the embodiment of FIG. 1, the locking mechanism 38 includes a flange 40 which is integral with or well secured at the left end 33 of the rod 30 and whose surface 41, facing the left upright panel 22, is ridged or roughened to provide increased friction against the outer surface of panel 22. Tightening of the winged nut 44 on the threaded portion 46 on the right end 31 of rod 30 is designed to bring the washer 47 to bear against the outer surface 49 of the panel 20 in order to pull the flange 40, at the other end 33 of rod 30, against left panel 22. The rod 30 and hence the orientation of platform 24 will thus become locked.

A pair of glove inflating cylinders including a right cylinder 50 and a left cylinder 52 are rotatably supported at the upper surface 48 of the platform 24 in respective cups 58 and 60. The respective lower ends 54 and 56 of cylinders 50 and 52 are fitted relatively tightly—but slidingly—in the cups 58 and 60, with their bottom surfaces 66 and 68 slidable on the annular flanges 62 and 64 of cups 58 and 60. The center regions of the bottom surfaces 66 and 68 of the cylinders 50 and 52 are therefore exposed to the interior 70 of the hardware enclosure 16. Cups 58 and 60 may be affixed to the upper surface 48 of platform 24 by various means including adhesives, rivets, bolts or the like.

Thus mounted, glove inflating cylinders 50 and 52 are rotatable about their respective axes and/or tiltable to the front or back relative to a person facing the front wall 26 of machine 10.

A pair of gloves including a right hand glove 74 and a left hand glove 76 may be mounted to the openings 78 and 80 of the cylinders 50 and 52 by stretching and folding the cuff portions 82 of the gloves 74 and 76 around the rims 84 and 86 of the cylinders 50 and 52. This allows gloves 74 and 76 to be inflated to large sized gloves 75.

For inflating gloves 74 and 76, an air hose 88, disposed within the interior 70 of hardware enclosure 16, has one pair of ends 91 which are connected to the bottoms 66 and 68 of cylinders 50 and 52, preferably through rotation-permitting couplings 90. The other end 92 of air hose 88 is connected to a pneumatic switch 94 and, via the switch 94, to a pump 96 that is coupled to switch 94 by pressure line 98 and a vacuum line 100. Pneumatic switch 94 and pump 96 are controlled by respective electrical outputs transmitted to them via electrical harness 102 from an electrical controller 104.

Electrical controller 104 can receive and is controlled by several or all of the following inputs (depending on the number of inputs made available) including:

(1) AC power from electrical plug 106 via AC lines 108 and ON/OFF switch 110.

(2) A momentary START signal for activating the pump 96 for a set period of time. The START signal may originate from: the START switch 112 on platform 24 via lines 114; the START lever 116 of pedal 118 via lines 120; and/or from glove actuated microswitches 122 (FIG. 5) disposed within cylinders 50 and 52 and coupled to controller 104 via lines 124.

(3) A TIMER signal originating from an adjustable TIMER 138 on the right upright panel 20, via lines 140. As noted above, the pump 96 is energized for a set period in response to activation of any of the START switches (112, 116 or 122). That time period may be adjusted by means of the TIMER 138.

Figure 5:
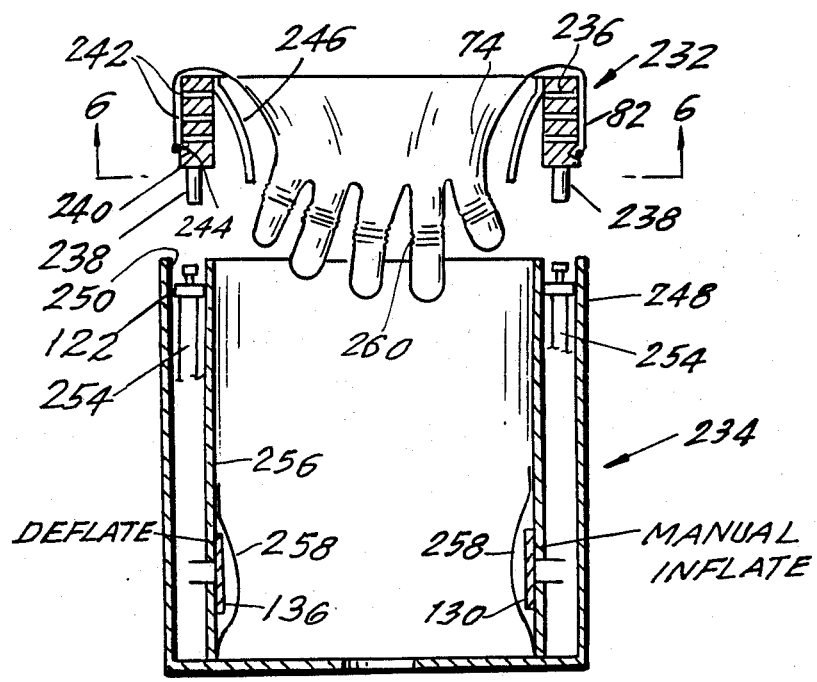
FIG. 5 depicts a novel glove assembly in which a glove comes prefitted on a special expansion ring for facilitating mounting of a glove to the inflating cylinder.

(4) A MANUAL INFLATE signal for energizing the pump 96 during the activation of any of: the MANUAL INFLATE switch 126 on platform 24; the MANUAL INFLATE lever 128 of the pedal 118; or the MANUAL INFLATE switch 130 disposed within cylinders 50 and 52 (FIG. 5).

(5) A DEFLATE signal for restoring atmospheric conditions and/or for generating an elevated pressure within cylinders 50 and 52 to allow the inflated gloves 75 to shrink about a person's hands. The DEFLATE signal may originate from: the DEFLATE switch 132 on platform 24; the DEFLATE lever 134 of pedal 118; and/or, as is preferred, from the internally located DEFLATE switch 136 of cylinders 50 and 52 (FIG. 5).

Although multiple signal sources have been described above for generating the inputs to controller 104, in its simplest configuration, the present invention requires only a single signal of either the START or MANUAL INFLATE type for inflating the gloves 74 and 76 and only a single DEFLATE signal for causing the gloves to deflate on a person's hands.

Preferably, the START signals are momentary signals which when transmitted to electrical controller 104 result in the energization of pump 96 for a set, but adjustable, time duration controlled by timer 138. Typically, timer 138 should be set to provide an average glove inflating period and, therefore, a standard inflated glove size. But it is possible for any person and particularly a person having larger hands to use the MANUAL INFLATE switches 126, 128 or 130 instead of or in addition to the START switch to inflate the gloves 74 and 76 to obtain greater glove inflation.

Thus, donning of a pair of gloves 74 and 76 with the system 12 can proceed rapidly and easily by the following procedure. A glove 74 or 76 is retrieved from a glove package (not shown) and, while the hand portion of the glove 74/76 is allowed to hang into the cylinders 50 and 52, the cuff portions 82 thereof is stretched and folded over the rims 84 or 86 of cylinders 50 and 52. Any one of the START switches 116, 112 or 122 (depending on the particular embodiment) may then be actuated to energize the pump 96, thereby to create a negative pressure within the interiors of cylinders 50 and 52, via the vacuum line 100, the pneumatic switch 94 and air hose 88. Atmospheric air rushing into the gloves 74 and 76 will then inflate the original unstretched gloves 74 and 76 to the enlarged gloves 75. The size of enlarged gloves 75 is adjustable by means of timer 138.

It is also possible to increase the size of the inflated gloves 75 by depressing any of the MAN INFLATE switches 126, 128 or 130 to obtain further pump energization and greater glove inflation.

The final step requires a person to insert both hands into the expanded gloves 75 and, with his/her hands comfortably positioned within the gloves 75, to press the DEFLATE switches 136 within cylinders 50 and 52. This restores atmosphere conditions within the cylinders 50 and 52 and results in a rapid shrinking of the gloves 75 about the person's hands. The gloved hands may then be simply lifted out of cylinders 50 and 52.

In a more elaborate embodiment of the invention, activation of any of the DEFLATE switches 132, 134 or 136 also produces further outputs on lines 102 of controller 104. The further outputs energize the pump 96 and control switch 94 to connect the pressurized air line 98 of pump 96 to the interior of cylinders 50 and 52, via air hose 88. This will produce an elevated pressure within cylinders 50 and 52 that will blow the cuff portion 82 of the gloves 74 and 76 off the rims 84 and 86 of the cylinders 50 and 52.

The present invention provides further cylinder embodiments which facilitate dislodging of the cuff portions 82 of gloves 74 and 76 from the rims 84 and 86 of cylinders 50 and 52. These further embodiments are illustrated in FIGS. 3, 4A, 4B, 4C and 5 and described below by reference to right cylinder 50.

Figure 3:
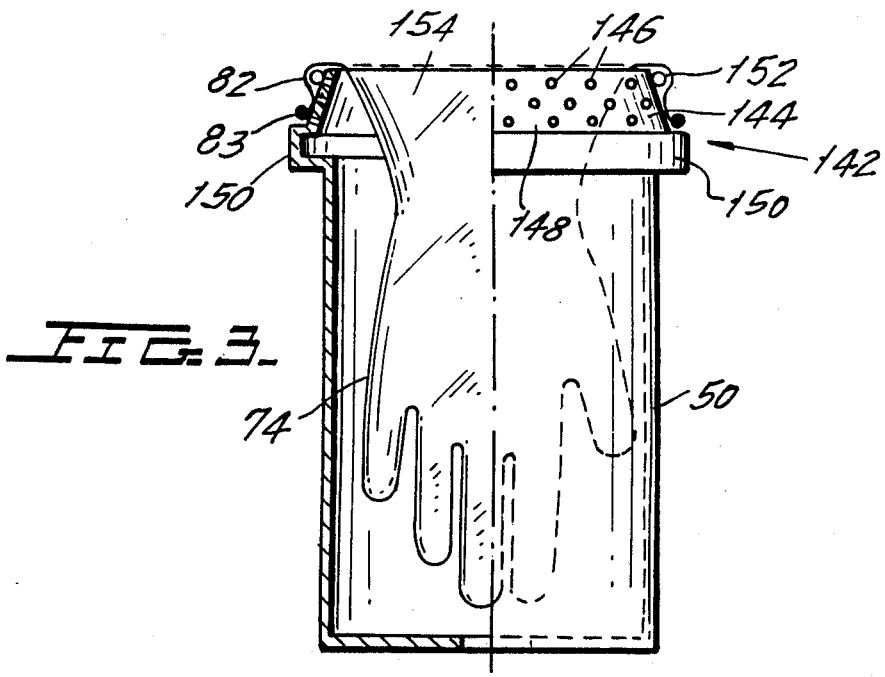
FIG. 3 is a cross-section through one of the glove inflating cylinders of FIG. 1 which has been modified to include a perforated rim for facilitating dislodging of the cuff portion of the glove from the rim of the cylinder after insertion of one's hand in an inflated glove.

Thus, in FIG. 3, the rim region 142 of the cylinder 50 includes a perforated frustoconical wall 144 with suction holes 146 and a radially projecting annular flange 150 at the base 148 of wall 144. Several beads 152 are preferably spacedly disposed along the upper circumferential periphery 154 of the rim region 142.

In the embodiment of FIG. 3, the cuff portion 82 of the glove 74 is mounted on the frusto-conical wall 144 with the outer thickened edge 83 of the cuff portion 82 abutting the flange 150. Stretching and mounting of the cuff portion 82 on the frusto-conical wall 142 is made easier by catching the edge 83 of cuff 82 on the beads 152. The surface area of the wall 144 and its cone angle are carefully dimensioned to allow relatively easy sliding of the cuff 82 off the frustoconical wall 144 in response to even slight downward pushing on glove 74.

During glove inflation, however, the vacuum created in the interior of the cylinder 50 acts through the suction holes 146 to firmly hold the cuff portion 82 on the rim region 142. However, at the time the DEFLATE signal is activated, a person's hands will be located in the inflated gloves 75 and the glove will thus be held relatively deep in the cylinders 50 and 52. Therefore, as the glove 75 shrinks it will be pulled down and the cuff 82 will slide off rim 142 and onto the persons's wrists.

In FIG. 3, it is also possible to reverse the pressure polarity in the cylinders 50 and 52 to cause the cuff 82 to pop off the rim 142, as described above in connection with FIG. 1.

In FIG. 4A, the rim region 156 of cylinder 50 includes several, arcuate and circumferentially spaced, cuff dislodging rods 158 that are pivotally connected at one end thereof by pivots 160 to the peripheral edge 162 at the cylinder opening 164. In response to a blast of air supplied through inlet 166 and channel 168 of cylinder 50 and directed at the rods 158 through apertures 170, the rods 158 is designed to swing radially out to dislodge the cuff 82 from the rim 156.

The rods 158 may be constructed as a plurality of overlapping plates which slide over and overlap one another sufficiently so that the plates remain overlapped even in the fully swung out position of the plates 158. The rod plates are, in other words, arranged and shaped like the plates in familiar variably sized vegetable steamers. Further, the plates 158 may be perforated and a negative pressure may be generated in the channels 168 during glove inflation for more firm holding of the glove 74. The rods 158 may also be mechanically coupled to a piston arrangement (not shown) in the channel 168 for effecting swinging of the rods 158.

In the cuff dislodging embodiment of FIG. 4B, the rim 172 of cylinder 50 includes one or more cuff dislodging pins 174 which move vertically up and down in vertical slots 176 that are defined in an L-shaped skirt 178 which hangs down from the outer edge 180 of a flange 182. The pins 174 are supported by a holding member 188 located in the space 184 between the wall 186 of cylinder 50 and the L-shaped skirt 178. Holding member 188 is biased up toward the flange 182 by a spring 190 which is anchored on the short leg 192 of the L-shaped skirt 178. A locking arm 194, connected to and hanging down from the holding member 188, includes a finger 196 for grasping a tab 198 on the exterior of the wall 186 of cylinder 50 to hold the pin holding member 188 down and the spring 190 compressed as shown at the right side of FIG. 4B. In this position, the cuff 82 of glove 74 can be tightly fitted around the skirt 178 to allow the glove to be inflated.

With one's hand in the inflated glove 75 it is possible to press the button 200 to thereby push the locking arm 194 radially out, away from the locking tab 198. This then frees the spring 190 and allows the pins 174 to impelled upward to at the same time dislodge the cuff 82 off the rim 172. The button 200 is biased toward the interior of the cylinder 50 by spring 202 and, moreover, buttons 200 may be covered by a membrane 204 to seal the interior and, therefore, the vacuum of cylinder 50 from air leaks. Beads 160 may be advantageously added in the present embodiment to facilitate mounting of the cuff portion 82 of glove 74 on the rim 172.

In the embodiment of FIG. 4C, a relatively short tube 206 having an outer diameter which closely matches the inner diameter of the cylinder 50 is slidingly fitted at the upper end 208 of cylinder 50. A rim section 210 of tube 206 projects beyond the peripheral wall edge 211 of cylinder 50. The bottom 212 of the tube 206 rests on one or more springs 214 which springs 214 are anchored on ledges 216 which project radially in from the inner wall surface 218 of cylinder 50. A hand lever 220 hangs down from tube 206, reaching below the fingers 222 of inflated glove 75 and terminating in a handle 224. The handle 224 is designed to be pressed down to draw the tube 206 and its rim section 210 into the cylinder 50. Consequently, as the rim section 210 disappears into the cylinder 50, the cuff 82 fitted on rim section 210 will be dislodged therefrom.

Preferably, the tops 226 of the springs 214 form an annular sliding surface for the bottom 212 of tube 206 to allow the tube 206 to rotate about the axis 228 of cylinder 50. Further, cuff stops 230 which protrude radially from the wall of cylinder 50 may be advantageously provided as shown to assure proper and consistent mounting of cuff 82 on rim section 210. The present embodiment thereby dispenses with both the cups 58 and 60 and the rotation-permitting couplings 90 for air hose 88 (FIG. 1). The cylinders 50 and 52 may then be firmly, and therefore more easily, secured to platform 24.

In all the above embodiments, a degree of manual dexterity, time and effort is still required to mount the gloves 74 and 76 to the rims of cylinders 50 and 52. Glove donning is, however, significantly facilitated in accordance with the embodiment of FIG. 5, by providing a glove assembly 232 and a modified cylinder 234 which allow gloves 74 and 76 to be mounted to the cylinders 234 virtually without effort and in a matter of several, perhaps no more than about 2-3 seconds.

Each glove assembly 232 includes a glove 74 and an expansion ring 236 on which the manufacturer has premounted the cuff 82 of the glove 74. A pair of pins 238 project from the bottom 240 of the ring 236. Preferably, the pins 238 are circumferentially offset from one another by an angle other than 180° (FIG. 6) and a plurality of radially extending suction holes 242 penetrate the ring 236. An annularly extending groove 244 may be provided down on the exterior periphery of the ring 236 for receiving the thickened edge 83 of glove 74. To protect the suction holes from being blocked by glove 74, an arcuate, annularly extending, guard plate 246 projects inwardly of ring 236.

The glove assembly 232 is designed to be simply placed atop the wall 248 of cylinder 234 with the pins 238 aligned to and inserted in the pair of recesses 250 in cylinder 234. In each recess 250, the pins 238 activate a microswitch 122 which completes the circuit between wires 254. Preferably, the two sets of wires 254 (associated with the pair of microswitches 122) are connected in series with one another and such that a START signal is generated for electrical controller 104 (FIG. 1), but only when both microswitches 122 have been actuated.

Thus, in the embodiment of FIG. 5, a glove does need to be stretched to be mounted to a rim and placing of a glove assembly 232 on the cylinder 234 results in automatic inflation of gloves 74 and 76. Moreover, the ring 236 serves to properly orient the thumb and fingers of the gloves 74. The cylinder 234 can be, therefore, fixedly and, therefore, more simply mounted to the platform 24.

During glove inflation, the suction holes 242 serve to hold the cuff 82 by suction on the outer peripheral surface of the ring 236. Dislodging of the cuff portion 82 could be accomplished with either a blast of pressurized air or by any of the previously described means.

FIG. 5 also illustrates the MANUAL INFLATE switch 130 and the DEFLATE switch 136 which are provided within and on the interior wall surface 256 of cylinder 234. Both switches 130 and 136 are covered by a membrane 258 for protecting the cylinder 234 against air leaks. Switches 130 and 136 should, preferably, be disposed oppositely to one another to allow them to be easily actuated from within the cylinder 234 through simple reaching with one's fingers toward one or the other of the switches. Although described in connection with FIG. 5, locating at least the DEFLATE switch 136 within the inflating cylinder is generic to all the embodiments of the present invention.

Figure 6:
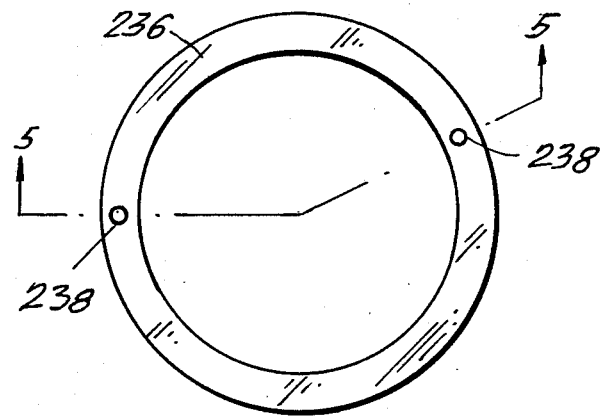
FIG. 6 is a bottom view of the glove assembly of FIG. 5 as seen along line 6—6.

The glove 74, in FIG. 6, is further characterized by the folds 260 on the fingers of the glove. The folds 260 in effect produce variable length glove fingers and permit persons with shorter fingers to obtain better glove fitting at their finger tips.

Figure 7:
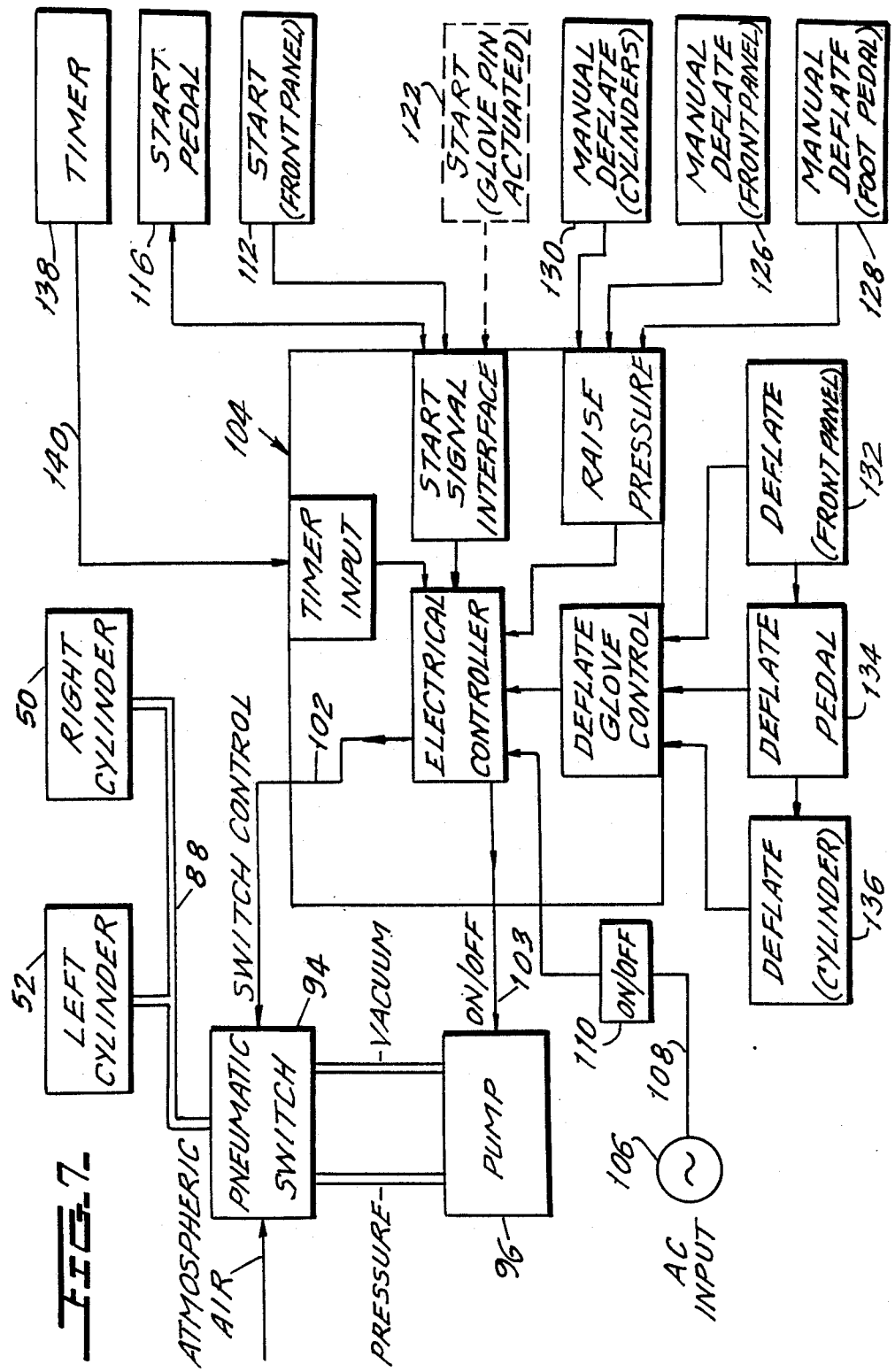
FIG. 7 is a general mechanical and electrical block diagram of the glove donning system of the present invention.

FIG. 7 is a general mechanical and electrical block diagram of the various embodiments of the present invention. The FIG. illustrates that the cylinders 50 and 52 are connected to pneumatic switch 94 through air hose 88 and that the pneumatic switch 94 is controlled by signals transmitted through control signal lines 102 in a manner that causes the switch 94 to couple either a negative pressure, a positive pressure or atmospheric pressure to air hose 88.

The electrical controller 104 comprises conventional electrical components such as relays and timing and control circuits which controllably apply electrical power through lines 108 to pump 96 in response to input signals which include the START, MANUAL INFLATE or DEFLATE signals. Conventional microprocessor, memory and associated hardware (not shown) may be used in controller 112 to receive the input signals and to generate the required outputs. The timer 138 may be a potentiometer and part of a simple RC circuit in the controller 112 for setting the energization duration of the pump 96—and hence the degree to which the glove is inflated—in response to any of the START signals.

Numerous additional improvements and refinements may be incorporated to enhance the general appeal and ease of use of the present invention. For example, the glove inflating cylinders 50 and 52 may be constructed in the shape of a hand of a person and the interior of the cylinders made visible by forming the cylinders of transparent plastic. Bearings 268 may be provided on the annular flanges 62 and 64 in FIG. 1 for smoother sliding of the bottoms 66 and 68 of cylinders 50 and 52 in the cups 58 and 60. Further, for most embodiments, the invention may be simplified by including only the vacuum (suctioning) capability. Also because, at times, it may be desired to don only one glove, a cylinder cover (not shown) may be supplied for covering the opening into the unused cylinder 50 or 52. Or, separate air hoses 88 may be routed from the switch 94 to the cylinders 50 and 52 to allow the air hoses 88 to be independently controlled. Further, the rear flexible wall 28 of hardware enclosure 16 may be replaced by a solid wall, if it is acceptable for the platform 24 to tilt only frontwise.

Referring to FIGS. 1 and 2, the glove removing system 14 of the present invention is housed in a lower hardware enclosure 270 and includes a pair of generally horizontally extending glove removing cylinders 272 and 274 into which a person wearing a pair of gloves may insert his/her hands for automatic removing of the gloves. Preferably, the glove removing cylinders 272 and 274 extend somewhat obliquely to the horizontal for more comfortable insertion of one's hands into the cylinders 272/274 while standing in front of system 14. Removed gloves 276 can be retrieved from the interior of the enclosure 270 through front door 278.

In accordance with a first and simpler embodiment (FIG. 2), each of the glove removing cylinders 272 and 274 is comprised of a short tube 280 having a hand insertion opening 282 and several resilient trapezoid shaped segments 284 which are resiliently and pivotably connected at their wider ends 286 (FIG. 1) at the opening 288 of the cylinders 272 and 274. The segments 284 extend both radially and axially into the interiors 292 of cylinders 272 and 274 such that the free edges 290 of the segments 284 define a hand insertion opening 294 having a diameter of a very small wrist of a person.

In operation, inserting one's hand into the opening 294 will momentarily deflect the segments 284. But once the gloved hand had been inserted deep enough into the cylinder 272, the segments 284 will spring back around the wrist of the person behind the glove. As the person subsequently begins to withdraw his/her hand from the cylinder 272, the segments 284 will snag/catch the cuff 82 of the glove 74 and peel the glove off the person's hand and allow the removed glove to simply fall to the bottom 296 of the enclosure 270.

Figure 8:
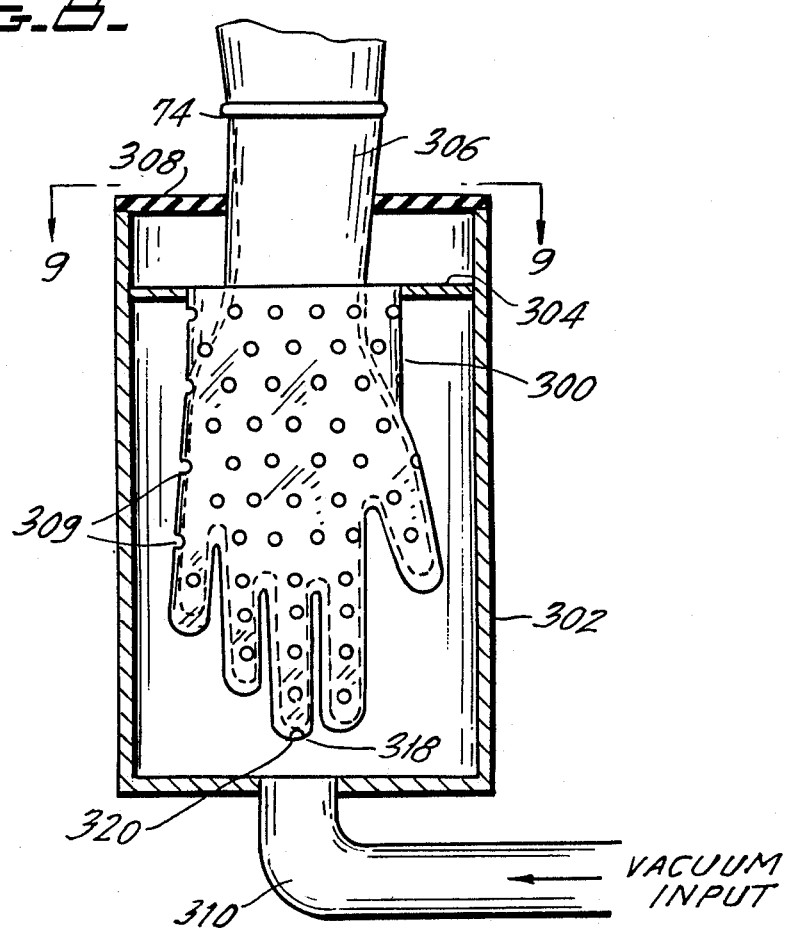
FIG. 8 is a cross-section through an embodiment of a glove removing cylinder in accordance with the present invention.
Figure 9:
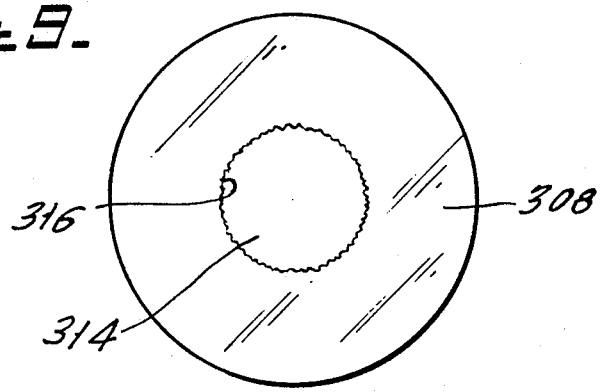
FIG. 9 is a top view of the glove removing cylinder of FIG. 8 along line 9—9.

A second glove removing cylinder embodiment comprises, as illustrated in FIGS. 8 and 9, a perforated hand form 300, disposed within a negative pressure cylinder 302, and secured to the cylinder 302 by a flange 304. The perforations 309 should be provided preferably over the entire hand form 300. Consequently, as a person inserts his gloved hand 306 through the rubber diaphragm 308 and into the hand form 300, the glove 74 will be drawn away from the person's hand as a result of a negative pressure established in the cylinder 302 through vacuum input 310. This will enable the person to free his/her hand from the glove.

The negative pressure may be supplied to cylinder 302 from pump 96 in hardware enclosure 16, via vacuum lines 312 (in the case where the systems 12 and 14 are integrated) or from a separately provided pump (not shown).

The diameter of the opening 314 (FIG. 9) in diaphragm 308 should be slightly smaller than a small wrist of a person. However, because the diaphragm 308 is made of rubber or a similar stretchable material, it is possible for a person to insert his/her hand through the diaphragm 308. By adhering to the wrist of the person the diaphragm 308 serves to seal the interior—that is the vacuum—of the hand form 300 from ambient air. It may be necessary to make the surface opening 316 jagged to allow some air penetration between the cuff of the glove and the wrist of the person to allow the glove 74 to become inflated.

A vacuum starting switch 318 and associated wires 320 may be disposed within the hand form 300 to start the pump 96 by finger actuation.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A glove donning machine, comprising:
   at least one glove inflation cylinder defined about an axis and having a hand insertion opening;
   a rim at the hand insertion opening for mounting a cuff portion of a glove thereon;
   inflating means for producing a negative pressure in the cylinder to inflate a glove mounted to the rim;
   a support for supporting the at least one cylinder on a surface; and
   a pivoting mechanism secured to the support, the cylinder being coupled to the pivoting mechanism in a manner that enables pivoting of the cylinder about its axis.

2. The machine of claim 1, the support comprising a base, the pivoting mechanism including a pivotable platform disposed above the base for mounting the at least one inflation cylinder thereon.

3. The machine of claim 2, wherein the pivoting mechanism further includes a pivoting rod and the platform is secured to the pivoting rod and the rod is rotatable to pivot the platform.

4. The machine of claim 3, further including at least one flexible wall which extends between the platform and the base.

5. The machine of claim 1, wherein the inflating means comprises a pump and air hose means for connecting the pump to the interior of the at least one cylinder and including control means for selectively energizing the pump to produce the negative pressure and for selectively releasing the negative pressure in the at least one cylinder.

6. The machine of claim 5, wherein the control means comprises first switch means for initiating actuating of the pump.

7. The machine of claim 6, in which the control means includes second switch means for initiating releasing of the negative pressure.

8. The machine of claim 7, wherein the second switch means is disposed within the at least one cylinder and is suitable for being actuated by a gloved hand of a person that is disposed within the interior of the at least one cylinder.

9. The machine of claim 8, further comprising membrane means disposed over the second switch means to provide protection against air leaks.

10. The machine of claim 7, wherein the control means includes timer means for energizing the pump for a predetermined time period in response to actuation of the first switch means.

11. The machine of claim 7, the first and second switch means comprising a foot pedal.

12. The machine of claim 7, the inflating means comprising a pneumatic switch coupled to the pump and disposed between the pump and the air hose means.

13. The machine of claim 1, wherein the at least one inflating cylinder comprises a first cylinder for holding a right handed glove and a second cylinder for accommodating a left handed glove and wherein the first and second cylinders are effective for enabling simultaneous inflating of a pair of gloves.

14. The machine of claim 1, further comprising rotation means for rotatably mounting of the at least one cylinder to the support.

15. A glove donning machine, comprising:
    at least one glove inflating cylinder defined about an axis and having a hand insertion opening;
    a rim at the hand insertion opening for mounting a cuff portion of a glove thereon;
    inflating means for producing a negative pressure in the at least one cylinder to inflate a glove mounted to the rim;
    control means for selectively energizing the inflating means to produce the negative pressure and for selectively releasing the negative pressure in the at least one cylinder; and
    glove dislodging means for dislodging the cuff portion of a glove that had been mounted to the rim.

16. The machine of claim 15, wherein the glove dislodging means comprises at least one pin that is movable from a first to a second position in a manner that is effective to dislodge the cuff portion of a glove off the rim.

17. The machine of claim 16, wherein the glove dislodging means includes push button means actuatable from within the interior of the at least one cylinder and the push button means is effective for initiating movement of the at least one pin from the first to the second position.

18. The machine of claim 15, wherein the glove dislodging means includes at least one pivotally mounted rod at the rim of the at least one cylinder, and means for pivoting the at least one pivotally mounted rod between first and second positions and in a direction to cause the cuff portion of a glove to be dislodged off the rim.

19. The machine of claim 15, wherein the glove dislodging means comprises a perforated wall at the rim for mounting the cuff portion of a glove thereon and for holding the cuff portion with suction during glove inflation.

20. The machine of claim 19, wherein the perforated wall is frustoconically shaped.

21. The machine of claim 15, wherein the rim comprises a plurality of circumferentially spaced beads which are effective for facilitating mounting of a cuff portion of a glove on the rim.

22. The machine of claim 15, wherein the glove dislodging means comprises a tube disposed within and partially projecting from the least one cylinder, the projecting portion of the tube defining the rim for mounting of the cuff portion of a glove thereon and including means for pulling the tube axially and in a direction that is effective to draw the projecting portion of the tube within the at least one cylinder.

23. The machine of claim 15, wherein the glove dislodging means comprises means for producing an elevated pressure within the at least one cylinder to dislodge the cuff portion of the glove from the rim by application of positive pressure.

24. The machine of claim 15, wherein the rim comprises a detachable ring for mounting the cuff portion of a glove thereto, the detachable ring including projecting pin means for engaging that at least one cylinder, the at least one cylinder including pin receiving recesses in registration with the pin means on the ring.

25. The machine of claim 24, further comprising switch means in the at least one cylinder which are positioned to be actuated by the pin means on the ring when the ring is mounted to the at least one cylinder, and wherein the switch means is effective for initiating energizing of the inflating means.

26. A glove assembly, comprising:

a ring for supporting the cuff of a glove thereon, the ring including at least one pin protruding from the ring for aligning the ring to a glove inflating cylinder.

27. The glove assembly of claim 26, wherein the at least one pin comprises a plurality of pins and the pins are spaced from one another in a manner that permits only a single manner in which the glove assembly may be mounted to a glove inflating cylinder.

28. The glove assembly of claim 27, wherein the ring comprises suction holes for holding, by suction, the cuff portion of a glove to the ring during glove inflation.

29. The glove assembly of claim 26, further including a glove mounted to the ring and the glove including pleated finger regions for producing a glove having fingers of variable length.

30. A glove donning machine, comprising:
at least one glove inflating cylinder defined about an axis and having a hand insertion opening;
a rim at the hand insertion opening for mounting a cuff portion of a glove thereon;
inflating means for reproducing a negative pressure in the at least one cylinder to inflate a glove mounted to the rim; and
control means for selectively energizing the inflating means to produce the negative pressure and for selectively releasing the negative pressure in the at least one cylinder;
the control means including switch means for initiating releasing of the negative pressure and the switch means being disposed within the at least one cylinder and being suitable for being actuated by a gloved hand of a person that is disposed within the interior of the at least one cylinder.

31. A glove removing machine, comprising:
a pair of glove removing cylinders for enabling a person to insert his/her hands into the cylinder to remove a pair of gloves from the person's hands simultaneously.

32. The glove removing machine of claim 31, wherein each of the glove removing cylinders comprises a cylindrical section having a hand insertion opening and a plurality of resiliently biased and radially inwardly directed segments at the hand insertion opening, the segments being effective to enable a person to insert his/her hands therethrough and, when the person withdraws his/her hands from the cylinders, to snag the cuff portions of gloves and to remove the gloves from the person's hands.

33. The glove removing machine of claim 31, wherein each of the glove removing cylinders respectively comprises an outer cylinder, a perforated hand form within the outer cylinder, means for generating a negative pressure between the outer cylinder and the perforated hand form whereby upon the insertion of a gloved hand into the hand form the glove is drawn away from the person's hand.

34. The glove removing machine of claim 33, wherein each of the glove removing cylinders further comprises a diaphragm constructed of a flexible material and having a small central opening of a size that is effective for maintaining a negative pressure created between the outer cylinder and the hand form.

35. A glove donning machine, comprising:
at least one glove inflating cylinder for mounting a glove in the at least one glove inflating cylinder for inflating the glove to enable a person to insert his/her hand in the glove; and
at least one glove removing cylinder effective for removing a glove from a person's hand when a person inserts his/her hand into the glove removing cylinder and thereafter removes his/her hand from the glove removing cylinder.

* * * * *